US00PP11141P

United States Patent [19]

van der Meer

[11] Patent Number: Plant 11,141

[45] Date of Patent: Dec. 7, 1999

[54] HYBRID TEA ROSE PLANT NAMED 'SELRUTHENIUM'

[75] Inventor: Peter Johannes Antonius van der Meer, Carpinteria, Calif.

[73] Assignee: Terra Nigra Holding B.V., Netherlands

[21] Appl. No.: 09/048,205

[22] Filed: Mar. 26, 1998

[51] Int. Cl.[6] ..... A01H 5/00

[52] U.S. Cl. ..... Plt./130

[58] Field of Search ..... Plt./130, 131, 135, Plt./136

*Primary Examiner*—Howard J. Locker

[57] ABSTRACT

A new rose variety of the Hybrid Tea class, characterized by its continuous good production of orange yellow flowers which start pink still in bud, turn more orange when opening up, and when aging become more yellow, having a very good presentation, borne singly on upright stems on a bush of medium height (90–140 cm), and beautiful dark green foliage of good quality.

1 Drawing Sheet

BACKGROUND OF THE INVENTION

The present invention relates to a new and distinct variety of rose plant of the Hybrid Tea class, which was originated by me by crossing Domingo with unnamed seedling 90.036.

The female parent Domingo differs from the present invention by color (yellow throughout) and in the number of petals (21–30 petals per flower). The male parent 90.036 is a bi-color yellow and red, does not have a fragrance, has many thorns and a bad leaf quality. The male parent has not been available outside TERRA NIGRA B.V..

The primary objective of this breeding was to obtain a new yellow large type rose with a good presentation and budshape. Among the novel characteristics possessed by the new variety which distinguish it from its parents and all other varieties of wihch I am aware are:

1) A very large flower and flowerbud.

2) The color combination of the flower.

3) A vigorous growth of the plant of medium height (90–140 cm).

4) Very strong stems.

5) Good quality dark green leaves, which retain this color in the vase.

Asexual reproduction of the new rose variety by cutting and grafting using Natal Briar as rootstock, as performed in a greenhouse in De Kwakel, The Netherlands, shows that the aforementioned characteristics and distinctions come true to form and are established and transmitted through succeeding propagations.

BRIEF DESCRIPTION OF THE DRAWINGS

The new variety of rose plant is illustrated by the accompanying photographic illustrations, of which.

Figure 1:
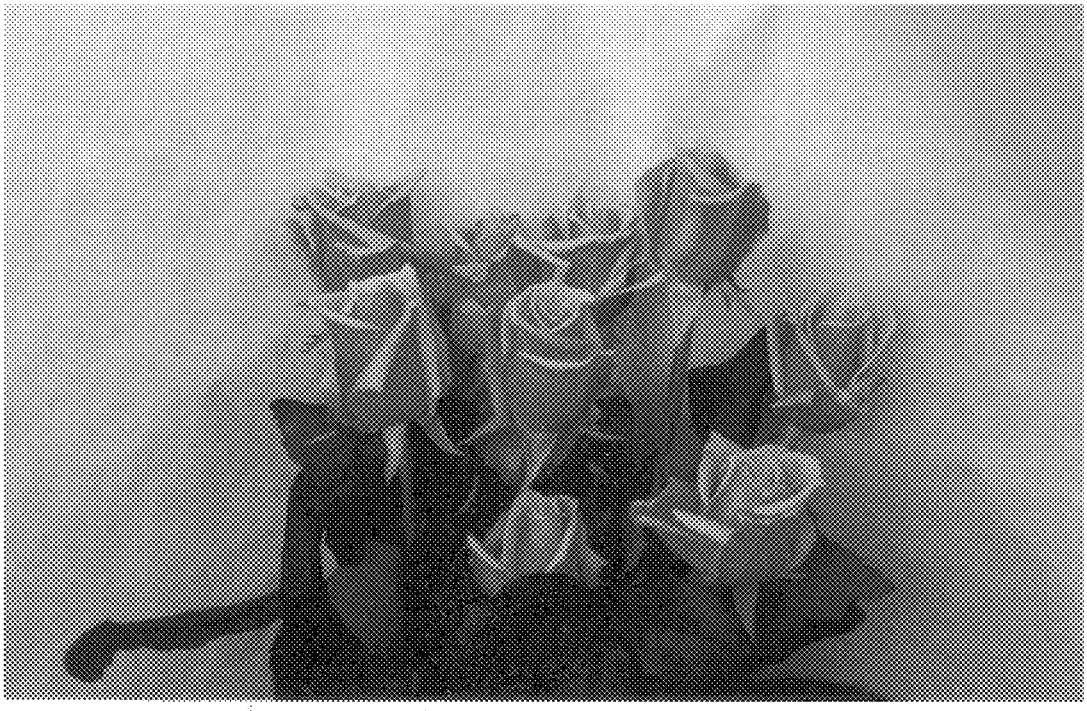
FIG. 1 shows typical blooms and foliage of the cultivar.
Figure 2:
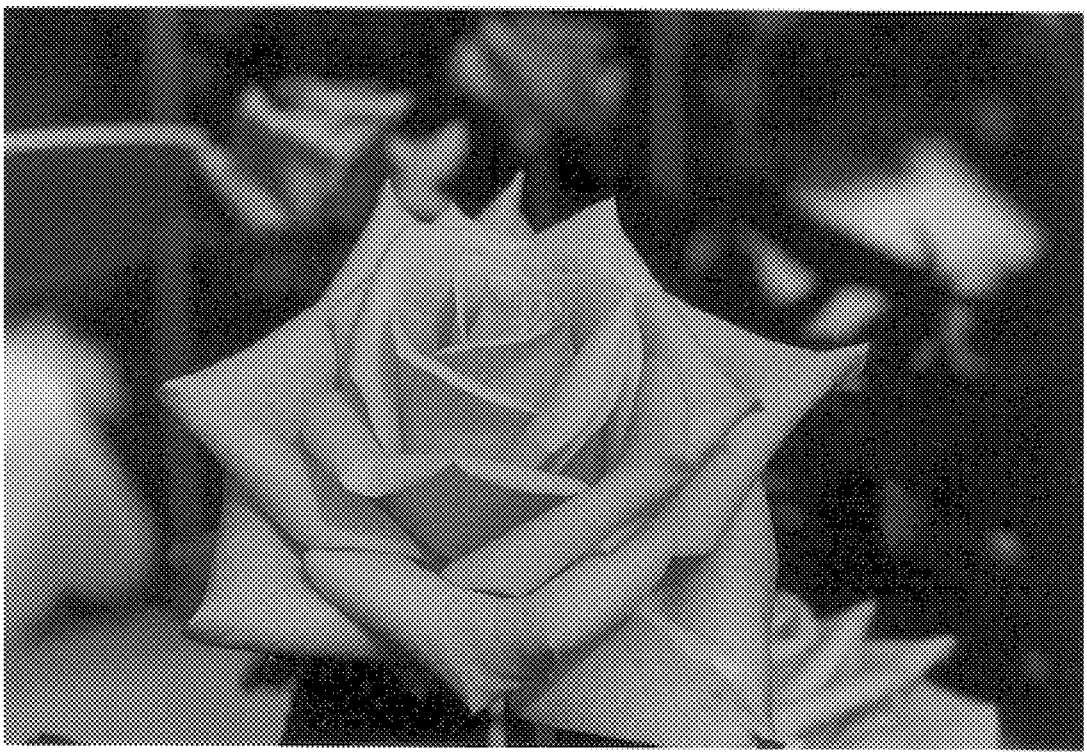
FIG. 2 is a close up view of an open bloom.

The colors set forth in the illustrations are as true as is reasonably possible to attain in color illustrations of this type.

The following is a detailed description of this new variety, with color terminology in accordance with The Royal Horticultural Society Colour Chart (R.H.S.C.C.). The terminology used in the color description herein refers to plate numbers in the aforementioned color chart e.g "55C" is plate "55C" of The Royal Horticultural Society Colour Chart.

Parentage: Seedling.

*Seed parent*.—Domingo.

*Pollen parent*.—Unnamed seedling 90.036.

Classification:

*Botanic*.—Rosa hybrida.

*Commercial*.—Hybrid Tea.

BOTANICAL DESCRIPTION OF THE PLANT (Observations made from specimens grown in a greenhouse in De Kwakel, The Netherlands, Feb. 19, 1998, 9.00 a.m.).

FLOWER

Blooming habit of 'Selruthenium': Almost continuous.

A. Bud:

(1) *Size*.—Large. Diameter 28–32 mm. Length 50–55 mm.

(2) *Form*.—Pointed; is not affected by wet or hot weather.

(3) *Color*.—When the sepals first divide, the color of the outside is pinkish red, at base to middle (approx. 50%) R.H.S. 53B, at the edges R.H.S. 51B.

(4) *Sepals*.—Shape: 30 to 35 mm in length. Branched. Curl back when petals start to unfurl. Color: inside: R.H.S. 145A, at base (10%): R.H.S. 138B–C. outside: R.H.S. 146B.

(5) *Phyllaries*.—Number 8 per flower. Shape: 6–11 mm long and 1–4 mm broad. Color: red/brown, R.H.S. 181A.

(6) *Calyx*.—Color: R.H.S. 144B. Shape: pitcher. Size: large to broad. Aspect: smooth. Odor when rubbed: little present.

(7) *Rate of opening*.—Rapid.

(8) *Peduncle*.—Length: medium, 105 to 125 mm. Aspect: smooth. Strength: strong. Color: R.H.S. 144A, striped with R.H.S. 175A.

(8) *Opening*.—Opens up well; is not affected by adverse weather.

B. *Bloom:*

(1) *Size*.—Very large; when fully expanded about 14 cm in diameter with a depth of about 4 cm.

(2) *Borne*.—Single.

(3) *Stems*.—Length: medium to long (70–90 cm). Strength: very strong.
(4) *Form* (*when first open*).—Star shaped. Permanence: will flatten when aging.
(5) *Petalage*.—Number of petals: average 37.
(6) *Color*.—Center of flower: R.H.S. 24B. General tonality: yellow orange, R.H.S. 24B.
(7) *Discoloration*.—General tonality yellow orange, R.H.S. 24B aging to R.H.S. 22B.

C. Petals:
(1) *Texture*.—Leathery; is not affected by wet or hot weather.
(2) *Appearance*.—Inside: satiny. Outside: satiny.
(3) *Form*.—Broad obovate. very strong reflexing of margin, no or very weak undulation of margin.
(4) *Color*.—Inner side: Color of middle zone: R.H.S. 23B. Color of marginal zone: R.H.S. 23C. Spot at base: present. Size of spot at base: small (5 mm). Color of spot at base: R.H.S. 17C. Outer side: Color of middle zone: R.H.S. 34C. Color of marginal zone: R.H.S. 39B. Spot at base: present. Size of spot at base: small (4 mm). Color of spot at base: R.H.S. 12B.
(5) *Arrangement*.—Regular.
(6) *Petaloids in center*.—Number: average 3. Size: medium (approx. 1 cm by 1 cm). Color: base R.H.S. 12A, middle and marginal zone R.H.S. 24B spotted with R.H.S. 30A.
(7) *Persistence*.—Drop off cleanly.
(8) *Fragrance*.—Medium, sweet scent.
(9) *Lasting quality*.—On the plant: good. As cutflower: 8–10 days.

REPRODUCTIVE ORGANS

A. Stamens:
(1) *Arrangement*.—Regularly arranged around styles, outer ring above pistils.
(2) *Number*.—Average close to 170.
(3) *Length*.—9 to 11 mm.
(4) *Anthers*.—Size: large, 3 to 4 mm. Color: yellow, R.H.S. 12A; edges R.H.S. 22A.
(5) *Filaments*.—Length: large, 6 to 7 mm. Color: predominant color of filament: yellow. base of anthers R.H.S. 4A, edges R.H.S. 22A, lower filament yellow, R.H.S. 12B.
(6) *Pollen*.—Color: yellow.

B. Pistils:
(1) *Styles*.—Number: average close to 150. Length: medium (approx. 9 to 11 mm). Color: light yellow, R.H.S. 4D.
(2) *Stigmas*.—Color: light yellow, R.H.S. 4D.
(3) *Fruit*.—Fertiity: good. Shape: ovoid. Color at maturity: orange.

PLANT

A. Form: Greenhouse rose.
B. Growth: Vigorous.
C. Height: Medium, 90 to 140 cm.
D. Foliage: 11 compound leaves on bloom stem, 12 on main canes. Average 3 to 7 leaflets per compound leaf.
(1) *Size*.—Large.
(2) *Quantity*.—Abundant.
(3) *Color*.—New foliage: upper side: in between R.H.S. 135A and R.H.S. 137A. under side: R.H.S. 148C. Old foliage: upper side: R.H.S. 135A. under side: R.H.S. 148C.
(3) *Texture*.—Upper side: leathery. Under side: dull.
(4) *Terminal leaflet*.—Shape of base: obtuse. Size: large. Length: long (approx. 107–116 mm). Maximum width: broad (approx. 60 mm). Length petiole: medium (approx. 25 mm).
(5) *Ribs and veins*.—Ordinary.
(6) *Rachis*.—Upper side: brown, R.H.S. 183A. Lower side: light brown, R.H.S. 173C.
(7) Margin type.—Serrate, 3 points/cm, 2 mm peak.
(8) Stipules.—Length: average 18 mm, auricle to 6 mm. Texture: hairy. Color: Green, R.H.S. 137A.

E. Resistance to diseases: Average disease resistance.
F. Wood:
(1) *New wood*.—Color: Purple. Bark: smooth.
(2) *Old wood*.—Color: Dark green. Bark: smooth.

G. Thorns:
(1) *Quantity*.—Medium. On main stalks from base: medium. On laterals from stalk: few.
(2) *Form*.—Concave.
(3) *Length*.—Medium.
(4) *Hooked*.—Straight.
(5) *Color* (*when young*).—Red brown, R.H.S. 185A.
(6) *Position*.—Irregular.

H. Prickles:
*Quantity*.—Few. On peduncle: medium. On rachis: few (1).

I. Short needles:
*Quantity*.—Very few on peduncle.

I claim:

1. A new and distinct variety of rose plant of the Hybrid Tea class, substantially as herein shown and described, and characterized particularly as to novelty by its characteristics enumerated above.

* * * * *